Figure 1:
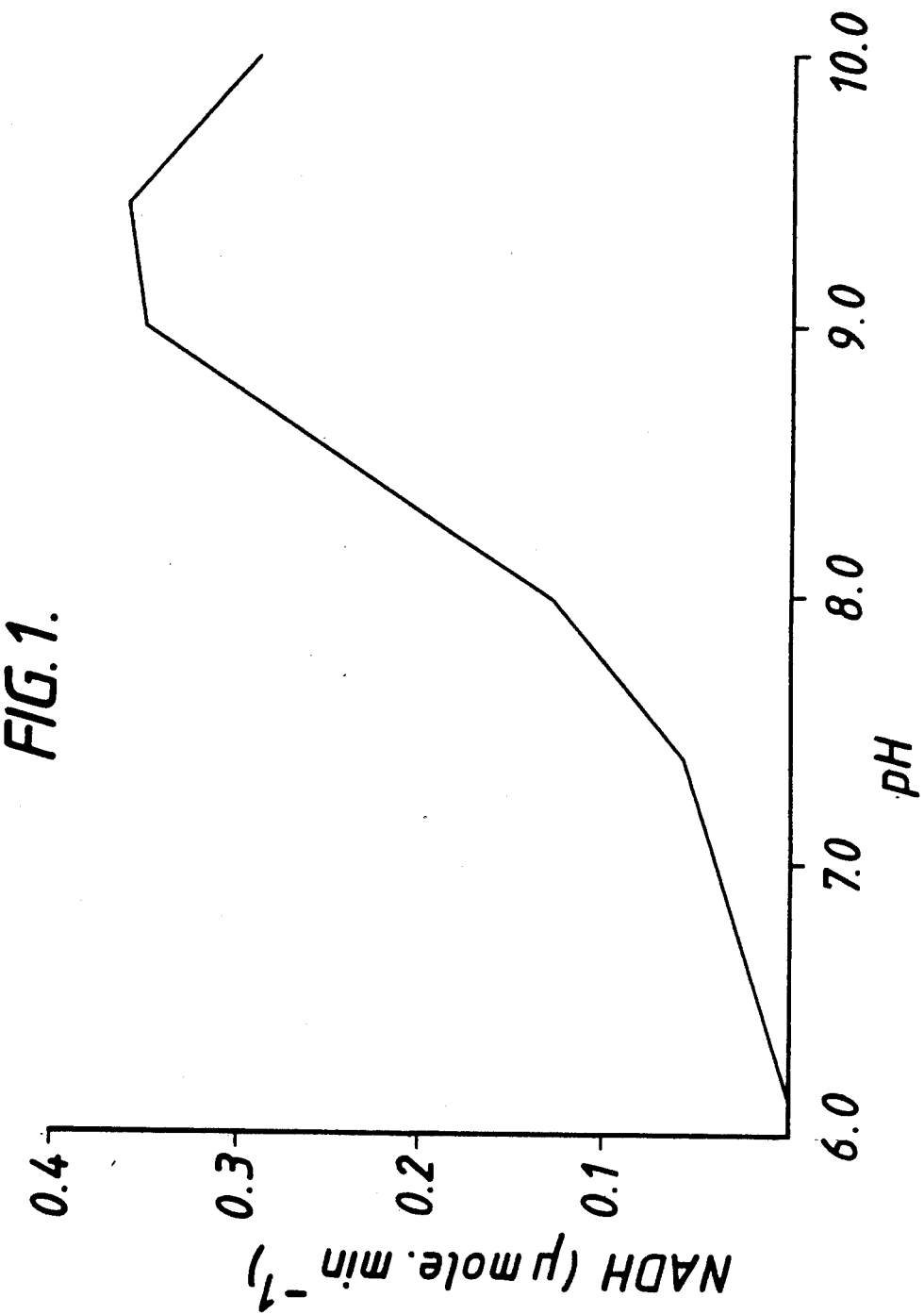

United States Patent [19]

Gisby et al.

[11] Patent Number: 5,002,886

[45] Date of Patent: * Mar. 26, 1991

[54] OXIDOREDUCTASE AND THE PREPARATION THEREOF

[75] Inventors: Paul E. Gisby, Surbiton; Roger D. Newell, London; Peter B. Park, Walton on Thames, all of England

[73] Assignee: British Gas PLC, London, England

[*] Notice: The portion of the term of this patent subsequent to Mar. 7, 2006 has been disclaimed.

[21] Appl. No.: 95,866

[22] Filed: Sep. 14, 1987

Related U.S. Application Data

[63] Continuation-in-part of Ser. No. 840,763, Mar. 18, 1986, Pat. No. 4,810,641.

[30] Foreign Application Priority Data

Sep. 15, 1986 [GB] United Kingdom ............... 8622714

[51] Int. Cl.$^5$ .............................................. C12N 9/04
[52] U.S. Cl. .................................. 435/190; 435/147; 435/158; 435/26
[58] Field of Search ................. 435/190, 147, 158, 26

[56] References Cited

U.S. PATENT DOCUMENTS

| | | | |
|---|---|---|---|
| 4,076,589 | 2/1978 | Charney | 195/49 |
| 4,342,827 | 8/1982 | Atkinson et al. | 435/26 |
| 4,395,489 | 7/1983 | Stahl et al. | 435/190 |
| 4,467,033 | 8/1984 | Horwath et al. | 435/105 |
| 4,734,366 | 3/1988 | Arena et al. | 435/105 |
| 4,810,641 | 3/1989 | Gisby et al. | 435/26 |

OTHER PUBLICATIONS

Andrejew, A. et al. (1978), Chem. Abst. 89:554004.
Martinez, G. et al. (1963), J. Biol. Chem. 238(5), 1598–1603.
Horwitz, S. B. et al. (1964) J. Biol. Chem. 239(3), 830–838.

*Primary Examiner*—Elizabeth C. Weimar
*Assistant Examiner*—Charles L. Patterson, Jr.
*Attorney, Agent, or Firm*—Larson and Taylor

[57] ABSTRACT

An oxidoreductase is provided which, in the presence of nicotinamide adenine dinucleotide (NAD$^+$) as a co-enzyme, will catalyse the oxidation of polyols having at least one hydroxyl group on each of at least two adjacent carbon atoms, e.g. 1,2-ethanediol. The enzyme has an apparent relative molecular mass $M_r$ of about 330,000 has substantially no specificity for monohydric alcohols and may be isolated from a micro-organism belonging to the genus Microbacterium.

2 Claims, 3 Drawing Sheets

OXIDOREDUCTASE AND THE PREPARATION THEREOF

This application is a continuation-in-part of U.S. application Ser. No. 06/840,763, filed Mar. 18, 1986, now U.S. Pat. No. 4,810,641.

This invention relates to the production of enzymes and to their use in biochemical assays. More particularly the invention relates to the production and use of oxidoreductases.

The dehydrogenase-catalysed oxidation of diols such as 1,2-ethane diol associated with concomitant hydrogenation or reduction of nicotinanide adenine dinucleotide (AND) has been known. For example, it has been reported that the dioldehydratase, propanediol hydrolyase, EC 4.2.1.28, will also catalyse the oxidation of 1,2-ethanediol to acetaldehyde [Abeles R H & Lee H A, Jr. 1961 J. Bio.Chem., vol. 236, pg. 2347]. Other enzyme systems known to catalyse reactions involving 1,2-ethanediol include alcohol oxidases (EC 1.1.3.X), AND(P) - linked primary alcohol oxidoreductases (EC.1.1.1.X), and dye-linked primary alcohol dehydrogenases (EC 1.1.99.X). Such systems cannot be used for the specific assay of one alcohol in the presence of others. This non-specificity of known alcohol dehydrogenase systems makes them unsuitable for use in certain industrial applications for example, the determination of 1,2-ethanediol (monoethylene glycol-MEG) in the presence of methanol. Both alcohols are present in natural gas. MEG is incorporated into the gas as a gas conditioner to ensure that the yarn employed in the jointing between pipe sections remains suitably swollen. Methanol is injected when the gas is first treated upon reception from the field to prevent formation of hydrates and may still be present in the pipeline gas. The determination of the MEG content of the gas is essential to ensure that sufficient conditioner is present to ensure the integrity of the distribution system.

We have found that the oxidation of certain polyols, including 1,2 ethane diol can be catalysed by novel dehydrogenase or oxidoreductase systems which are specific only for said polyols. The enzyme, which may be coupled with AND as the co-enzyme, may be obtained from microbiological sources.

The present invention accordingly provides, an oxidoreductase produced by a micro-organism belonging to the genus Microbacterium and characterised in that said oxidoreductase:
(a) will, in the presence of nicotinamide adenine dinucleotide compound as a co-enzyme, catalyse the oxidation of polyols having at least one hydroxyl group on at least two adjacent carbon atoms,
(b) has substantially no substrate specificity for monohydric-alcohols,
(c) has an apparent relative molecular mass $M_r$ of about 330,000 as measured on gradient gel electrophoresis,
(d) comprises eight protein sub-units, each of an apparent relative molecular mass $M_r$ about 41,000, as measured on sodium dodecyl sulphate gradient gel electrophoresis,
(e) has optimum activity at a pH of not less than 9.0,
(f) a stable pH range of 7.0 to 7.5,
(g) has an optimum temperature range of 30° C. to 45° C.,
(h) has a $K_m$ value for NAD+ of about 330 micromolar,
(i) has a $K_m$ value for 1,2-ethanediol of about 480 micromolar.

The Michaelis constants ($K^m$) for NAD+ and 1,2-ethanediol were calculated using the method described by Dixon, M and Webb, E.C. ("Enzymes", Longman Group Limited, 1964 pp. 84–86) for two substrate enzymes, based on data from primary plots constructed by the Lineweaver-Burke technique.

The oxidoreductase of the invention may be isolated from a culture of a microorganism, which has been partially identified as being of the genus Microbacteriu and which has been deposited with the National Collection of Industrial Bacteria, Aberdeen, Scotland under the accession number NCIB 12048, or from mutants and variants thereof.

The bacterium, on nutrient agar, forms white, round, low convex colonies, 2mm in diameter, after 4 days incubation at 30° C. On a defined medium containing 1,2 ethanediol as the sole carbon source, the bacterium forms off-white, entire, raised colonies of 2.0–2.5 mm diameter, after 7 days incubation at 30° C. The organism is Gram positive and is 3.0–4.0 um long by 1.5–2.00 um wide.

Thus the present invention also provides an oxidoreductase which, in the presence of a nicotinamide adenenine dinucleotide (NAD+) as a co-enzyme, will catalyst the oxidation of polyols having at least one hydroxyl group on each of at least two adjacent carbon atoms, obtained by isolation from a micro-organism belonging to the genus Microbacterium, together with a process for the production thereof which comprises cultivating a micro-organism belonging to the genus Microbacterium, in a culture medium containing carbohydrate, nitrogen source, and inorganic materials and recovering said oxidoreductase.

The oxidoreductase may be recovered and isolated from the micro-organism by standard preparative procedures. Thus, the bacterium cells may be first harvested by ultrafiltration techniques, or by continuous flow centrifuge techniques, followed by washing eg. by diafiltration. The harvested cells are then disrupted for example by mechanical or sonic disintegration techniques and the insoluble fractions removed therefrom, for example by filtration or centrifugation. Following concentration of the filtrate, the homogenous enzymatic material is recovered by precipitation from the filtrate, redissolved and isolated by, for example, elution from ion exchange chromatography columns.

The oxidoreductase has an apparent relative molecular mass $M_r$ of about 330,000. The molecular weight determination was effected by taking between 2 to 5 ug of the enzyme in 10 ul of a mixture of 20M Tris-HCl Buffer (pH 7.5)/ 0.1M NaCl and applying the sample to a pre-equilibrated polyacrylamide gradient gel (eg. Pharmacia PAA 4/30), with gel concentrations ranging from 4.0 to 30.0%. The protein will run as one band which can be observed by staining with bromophenol blue. The general conditions and reagents are described, for example, in the Pharmacia Handbook, "PAGE Electrophoresis". Following calibration of the gel with a molecular weight calibration kit, for example the Pharmacia electrophoresis high molecular weight kit, it was observed that the apparent relative molecular mass $M_r$ about 330,000.

The native protein of the enzyme is believed to comprise eight sub-units, each of an apparent molecular mass $M_r$ of about 41,000. This was determined by first equilibriating 2–10 ug of enzyme with a buffer containing Tris-HCl/NaCl, to pH 7.5, 1% w/v sodium dodecyl sulphate and 5% w/v B-mercaptomethanol, in a total volume of not more than 20 μl. The buffered sample was applied to a polyacrylamide gradient gel, eg. a Pharmacia PAA4/20 gel, and run in a discontinuous buffer system containing 0.2% sodium dodecyl sulphate. The enzyme runs as single band and when compared with a calibrated gel shows an apparent relative molecular mass $M_r$ of about 41,000, indicating that the enzyme protein comprises eight sub-units.

The oxidoreductase of the invention is highly specific for certain polyols. The evidence would suggest that in order to catalyse the oxidation of the polyol to the corresponding aldehyde at least one hydroxyl group must be present on each of at least two adjacent carbon atoms.

Substrate specificity tests were conducted to determine the catalyst activity in respect of selected polyhydric and monohydric alcohols, certain oxidation products thereof and the co-enzyme.

A reaction solution was made up comprising

| | |
|---|---|
| "CHES"* buffer (pH 9.0) | 100 millimolar |
| NAD+ | 100 millimolar |
| Substrate | 10 millimolar |

*2-(N-cyclohexylamino) ethane sulphonic acid.

To the reaction was added homogenous enzyme to make a final reaction volume of 1 cm³ of which 10% was enzyme. The reaction temperature was maintained at 25° C. The assay was effected by measuring the amount of NAD+ reduced to NADH, and the reaction is monitored by spectrophotometrically recording the absorbance between 338 and 340 nm over the period of 10-30 seconds after addition of the enzyme.

The following tables list the relative activities of a number of substrates assuming a value of 100% of 1,2-ethanediol which reacts according to the equation:

$$HOCH_2CH_2OH + NAD^+ \rightarrow HOCH_2CHO + NADH + H^+$$

| Substrate Formula | Name | Relative Activity % |
|---|---|---|
| HOCH₂CH₂OH | Monoethylene Glycol | 100 |
| HOCH₂CH₂OCH₂CH₂OH | Diethylene Glycol | 2.5 |
| HOCH₂CH₂OCH₂CH₂OCH₂CH₂OH | Triethylene Glycol | 0.5 |
| CH₃OH | Methanol | 0 |
| CH₃CH₂OH | Ethanol | 0 |
| CH₃CH(OH)CH₂OH | Propylene Glycol | 67 |
| HOCH₂CH(OH)CH₂OH | Glycerol | 142 |
| OHCCOOH | Glyoxylic Acid | 0 |
| OHCCH₂OH | Glycolaldehyde | 0 |

The optimum pH for the oxidation reaction may be from pH 9.0 to 9.5. However, because of the apparent chemical reduction of the NAD+ at high pH values, it is preferred to effect the polyol oxidation reactions at pH values at or near 9.0.

The pH profile of the oxidoreductase of the invention is shown in FIG. 1 of the accompanying drawings which is a plot of NADH production (by reduction of NAD+) with increasing pH.

Three reactant solutions were prepared as described above except that in two of the solutions, a buffer solution was replaced respectively with the following buffers:

| | |
|---|---|
| pH 6.1 | 150 millimolar "MOPS"* |
| pH 7.0-8.0 | 150 millimolar "HEPES"** |

*3-(N-morpholino) propane sulphonic acid
**N-2-hydroxypiperazine sulphonic acid

Reactions were carried out at 25° C. with a total reaction volume of 1 cm³ and adding enzyme (10% v/w) to the reaction solution.

Figure 2:
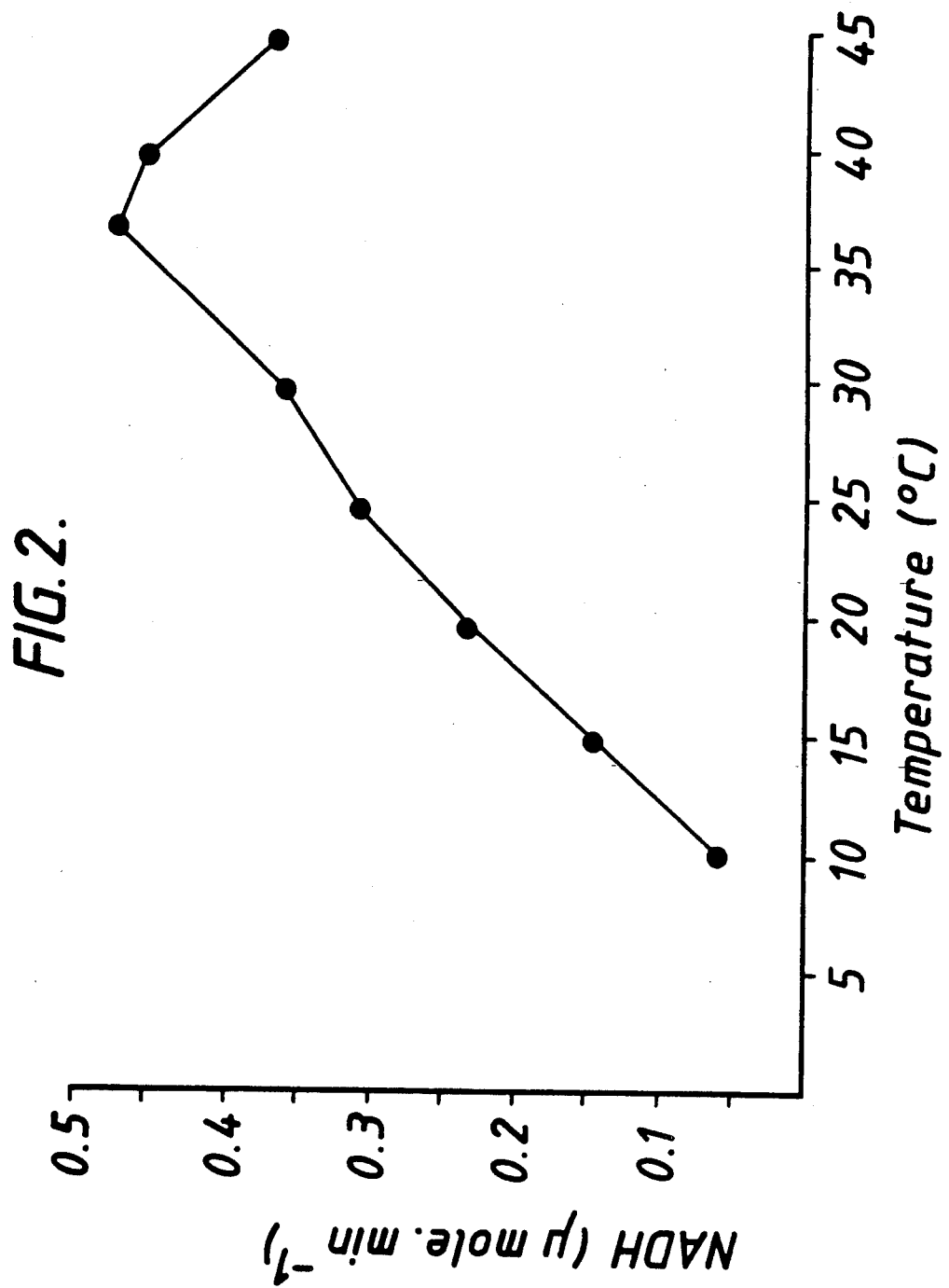

The temperature profile for the oxidoreductase of the invention is shown in FIG. 2 of the drawings and a plot of NADH produced against increase in temperature.

The reactant solution employed was:

| | |
|---|---|
| 100 mM | "CHES" Buffer (pH 9.0) |
| 10 mM | NAD+ |
| 10 mM | 1,2-ethanediol. |

The present invention will be further illustrated by reference to the following Examples:

EXAMPLE 1

Cells of Microbacterium SP. (NCIB 12048) were harvested from a fermenter by ultrafiltration in an Amicon Model DC 10L unit using a 0.1 um cut-off hollow fibre cartridge and the harvested cells washed with 5 volumes of 20mM Tris-HCl (pH 7.5).

After homogenisation in a Stansted Fluid Power Co. cell disintegrator, with the disruption chamber maintained at 41-42° C., the homogenate was immediately chilled to 4° C. and the insoluble residues removed by ultrafiltration. The enzyme is extracted by constantly diluting the residue in the filtration reservoir (i.e. diafiltration) using 20mM Tris-HCl (pH 7.5 buffer).

The enzyme-buffer solution thus obtained is concentrated to less than 1.5 litres passing the diluted solubilised homogenate through the Amicon DC 10L ultrafiltration unit using a 30,000 $M_r$ cut-off hollow fibre filter cartridge.

After concentration, the residue is treated with finely ground ammonium sulphate until the sulphate concentration is at 80% saturation and then the mixture is stirred for an hour and left overnight whilst maintaining the temperature at 4° C. The resulting mustard yellow coloured pellets are collected by centrifugation at 10,000x g; any white scum which is formed being discarded, and then dissolved in 100 cm³ of a 20mM Tris-HCl (pH 7.5) solution. The mixed solution is then diafiltered against four volumes of 20mM Tris-HCl (pH 7.5). The thus washed preparation is applied to a Whitman Ion Exchange DE52 column containing at least 200g of the gel, previously equilibrated with a mixed solution of 20mM Tris-HCl pH 7.5 and 200mM NaCl. The enzyme is eluted from the column with a gradient of 200-300 mM NaCl dissolved in the Tris-HCl buffer. The enzyme elutes between 260-280 ⓇM NaCl, and after pooling the fractions, is diafiltered against four volumes of the Tris-HCl buffer.

The washed eluate is concentrated by ultrafiltration until a concentrate is obtained containing at least two enzyme units cm⁻

Purification of the enzyme is effected by applying aliquots of the concentrate to the column of a TSK-DEAE-5PW HPLC, pre-equilibriated with the Tris-HCl/NaCl solution. Again, the enzyme is recovered in the 260-280aM salt solution when eluted against a gradient of 200-300 mM NaCl dissolved in the Tris-HCl buffer.

Active fractions are pooled and diafiltered against 4 volumes of 20mM Tris-HCl buffer (pH 7.5) containing 0.1 M NaCl, concentrated and subjected to gel filtration in column (50 ×2.6 cm) containing a pre-equilibriated gel (Pharmacia Sephacryl 5300). The active fractions from the column contain homogenous enzyme.

EXAMPLE 2

A variation of the procedure described in Example 1 was performed except that the harvesting procedure was effected by passing the broth from the fermenter through a continuous flow centrifuge rotor operating at 28,200 ×g, followed by cell disintegration by passage through a cooled continuous flow cell associated with a Branson Sonicator fitted with a micro-step horn, using a 50% duty cycle for 4-8 hours. Removal of the insoluble material from the homogenate is effected by passage through a continuous flow centrifuge rotor operating at 28,200 ×g.

Instead of diafiltration of the dissolved ammonium sulphate pellet, the preparation is dialysed against ten volumes of the 20mM Tris-HCI (pH 7.5) and the same dialysis step is repeated again for the eluate obtained from the DE52 column.

As a third method of treating the DE52 eluate, the fractions are diafiltered against four volumes of 20mM potassium dihydrogen phosphate/di-potassius: hydrogen phosphate buffer.

In an alternative to the HPLC treatment, the 2-unit concentrate can be applied to a column of chromatography grade hydroxyapatite, previously equilibriated with 20mM potassium di-hydrogen phosphate/di-potassium hydrogen phosphate buffer (pH 7.5). The enzyme is eluted against a gradient of between 20-200mM in sufficient purity not to require gel filtration.

The oxidoreductase of the invention may be used for biochemical assays. Accordingly, the present invention further provides a process for the biochemical assay of polyols having at least one hydroxyl group on each of at least two adjacent carbon atoms by the oxidation thereof which process comprises reacting said polyol with a nicotinamide adenine dinucleotide, at a pH of about 9.0 in the presence of an oxidoreductase in accordance with the invention.

The oxidoreductase of the invention is particularly, though not exclusively, suited for the determination of monoethylene glycol (1,2 ethane diol) in natural gas. Apart from having substantially no specificity for the other alcohols which may be present in the gas, the activity of the enzyme is not affected by other components of the gas e.g. mercaptans and sulphides which are used as odorants.

A 100 ml sample of natural gas was taken up from the distribution network into a cell. The gas contained 1,2-ethanediol of unknown concentration together with odorants comprising:

| | |
|---|---|
| ethyl mercaptan | 0.9 ppm |
| Tert-butyl mercaptan | 0.6 ppm |
| Other mercaptans | 0.1 ppm |
| Diethyl sulphide | 7.6 ppm |
| Methyl ethyl sulphide | 1.0 ppm |
| Ethyl isopropyl sulphide | 1.6 ppm |
| Other sulphides | 0.6 ppm |

Into the cell was injected cm$^3$ of a 2 millimolar solution of NAD and the whole was shaken vigorously for thirty seconds.

Figure 3:
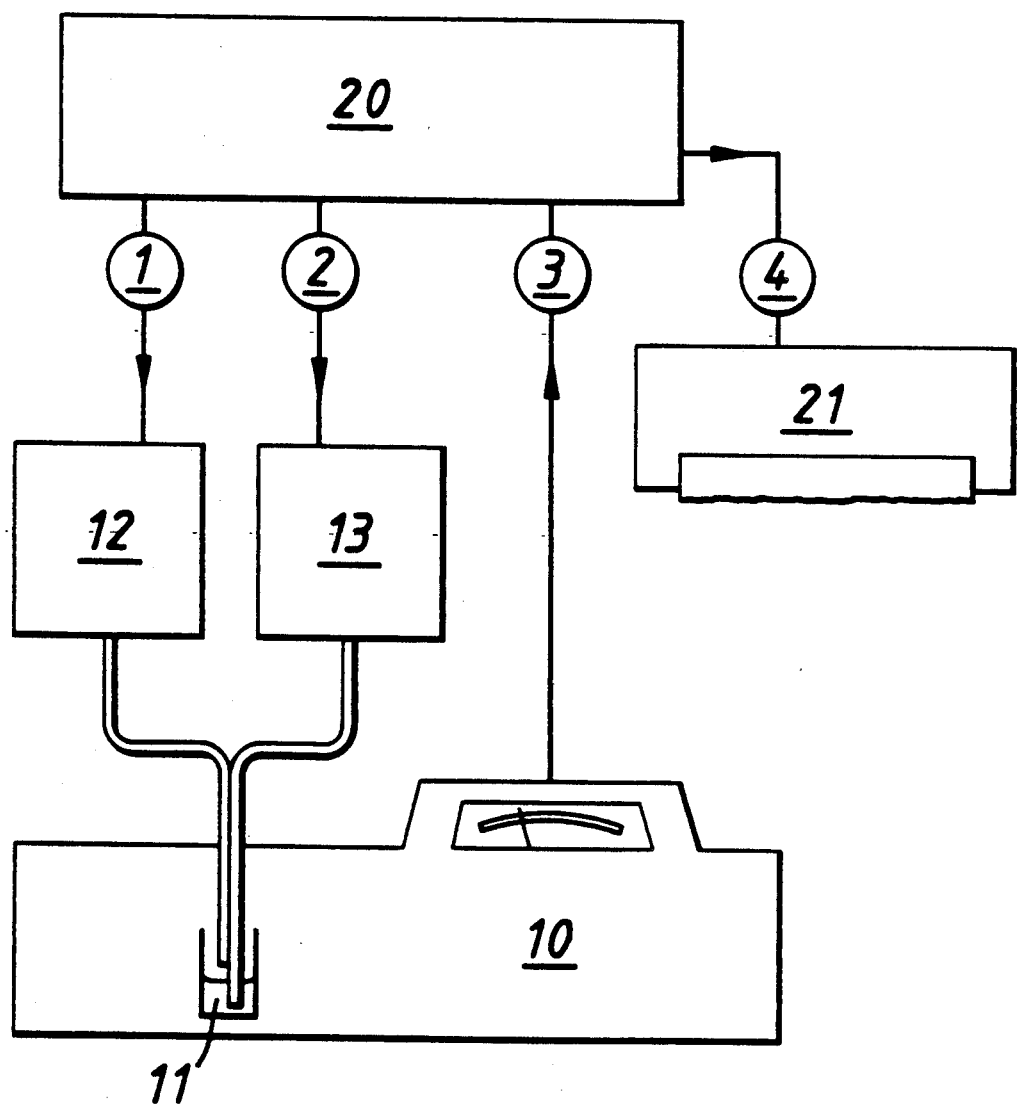

Referring to the FIG. 3 of the drawings, 0.9 cm$^3$ of the shaken solution was transferred to a reaction cuvette 11 of a Pye-Unicam SP6 Spectrophotometer 10, linked to a microprocessor 20 via line 3. The microprocessor also controls a liquid dispenser 12 and an air pump 13 via links 1 and 2, respectively.

Within the liquid dispenser is contained a solution containing the oxidoreductase in an initial concentration of 110 milliunits cm$^{-3}$. Prior to the assay the activity of the enzyme is determined to calibrate the instrument. This is done by assaying standard MEG solutions and plotting the change in absorbance per unit time against MEG concentration. These weighting factors are held within the microprocessor.

In testing for MEG in the test sample, 100 microlitres of the enzyme solution are added to the cuvette containing the shaken solution, after which air pumped in from pump 13 for three seconds to mix the reactants in the cuvette. The operation of the dispenser and pump are controlled by the microprocessor via links 2 and 3.

Once mixing has been completed a first absorbance reading is taken and recorded and, approximately six seconds later a second reading is made and recorded, the elapsed being accurately recorded by the microprocessor.

Using the data obtained from the calibrated test to weight previously inputed data on the rates of reaction, a calculation is performed on two measurements and the result, as a MEG concentration, of 5.40 mg m$^{-3}$ recorded with printer 21.

Transduction of NAD+ reduction (NADH production) may also be determined by amperometric methods using a platinum electrode coated with N-methyl phenazinium/7,7,8,8,-tetracyano-p-quinodimethane. This technique produces an electrode which will oxidize NADH (back to NAD+) and give a current proportional to the concentration of the reduced coenzyme. These electrodes for assaying reactions via the NAD-NADH couple are described in GB-A-26168815.

We claim:

1. A polyol dehydrogenase obtained from a microorganism of the genus Microbacterium which catalyzes the oxidation of polyols having at least one hydroxyl group on each of at least two adjacent carbon atoms to the corresponding aldehyde.

2. The polyol dehydrogenase of claim 1 wherein the microoganism is the Microbacterium species deposited as NCIB 12048 or mutants or variants having all the essential characteristics thereof.

* * * * *